(12) United States Patent
Libbus et al.

(10) Patent No.: US 8,010,198 B2
(45) Date of Patent: Aug. 30, 2011

(54) SYSTEMS AND METHODS FOR AVOIDING NEURAL STIMULATION HABITUATION

(75) Inventors: Imad Libbus, St. Paul, MN (US); Andrew P. Kramer, Marine on St. Croix, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 447 days.

(21) Appl. No.: 12/231,372

(22) Filed: Sep. 2, 2008

(65) Prior Publication Data

US 2009/0076561 A1 Mar. 19, 2009

Related U.S. Application Data

(60) Provisional application No. 60/972,154, filed on Sep. 13, 2007.

(51) Int. Cl.
*A61N 1/00* (2006.01)
(52) U.S. Cl. .......................................................... 607/44
(58) Field of Classification Search ...................... 607/44
See application file for complete search history.

(56) References Cited

U.S. PATENT DOCUMENTS

| | | | |
|---|---|---|---|
| 7,277,761 B2 | 10/2007 | Shelchuk | |
| 7,529,582 B1 * | 5/2009 | DiLorenzo | 607/2 |
| 2003/0018367 A1 | 1/2003 | DiLorenzo | |
| 2006/0015153 A1 | 1/2006 | Gliner et al. | |
| 2006/0079945 A1 | 4/2006 | Libbus | |
| 2006/0149337 A1 | 7/2006 | John | |
| 2006/0155348 A1 | 7/2006 | deCharms | |
| 2007/0142874 A1 | 6/2007 | John | |
| 2007/0162086 A1 | 7/2007 | DiLorenzo | |
| 2007/0167991 A1 | 7/2007 | DiLorenzo | |
| 2008/0033511 A1 | 2/2008 | Dobak | |
| 2008/0058871 A1 | 3/2008 | Libbus et al. | |
| 2008/0065158 A1 | 3/2008 | Ben-Ezra et al. | |
| 2008/0065167 A1 | 3/2008 | Boggs, II et al. | |
| 2008/0109050 A1 | 5/2008 | John | |

FOREIGN PATENT DOCUMENTS

DE 3405630 C1 6/1985

OTHER PUBLICATIONS

"International Application Serial No. PCT/US2008/010324, International Search Report mailed on Nov. 20, 2008", 3 pgs.
"International Application Serial No. PCT/US2008/010324, Written Opinion mailed on Nov. 20, 2008", 5 pgs.

(Continued)

*Primary Examiner* — George Manuel
(74) *Attorney, Agent, or Firm* — Schwegman, Lundberg & Woessner, P.A.

(57) ABSTRACT

An embodiment relates to a method for delivering a vagal stimulation therapy to a vagus nerve, including delivering a neural stimulation signal to non-selectively stimulate both afferent axons and efferent axons in the vagus nerve according to a predetermined schedule for the vagal stimulation therapy, and selecting a value for at least one parameter for the predetermined schedule for the vagal stimulation therapy to control the neural stimulation therapy to avoid physiological habituation to the vagal stimulation therapy. The parameter(s) include at least one parameter selected from the group of parameters consisting of a predetermined therapy duration parameter for a predetermined therapy period, and a predetermined intermittent neural stimulation parameter associated with on/off timing for the intermittent neural stimulation parameter.

28 Claims, 11 Drawing Sheets

OTHER PUBLICATIONS

"Australian Application Serial No. 2008297476, Examiner Report mailed Nov. 25, 2010", 2 pgs.

"European Application Serial No. 08830056.1, Communication mailed Apr. 21, 2010", 1 pg.

"European Application Serial No. 08830056.1, Response filed May 26, 2010 to Communication mailed Apr. 21, 2010", 19 pgs.

"Australian Application Serial No. 2008297476, Response filed Jun. 17, 2011 to Office Action mailed Nov. 29, 2010", 7 pgs.

* cited by examiner

SYSTEMS AND METHODS FOR AVOIDING NEURAL STIMULATION HABITUATION

CROSS REFERENCE TO RELATED MATTERS

This application claims the benefit under 35 U.S.C. 119(e) of U.S. Provisional Patent Application Ser. No. 60/972,154, filed on Sep. 13, 2007, which is incorporated herein by reference in its entirety.

TECHNICAL FIELD

This application relates generally to medical devices and, more particularly, to systems, devices and methods for delivering neural stimulation and avoiding physiological habituation to the neural stimulation.

BACKGROUND

Neural stimulation has been proposed as a therapy for a number of conditions. Examples of neural stimulation therapies include neural stimulation therapies for respiratory problems such a sleep disordered breathing, blood pressure control such as to treat hypertension, cardiac rhythm management, myocardial infarction and ischemia, heart failure, epilepsy, depression, pain, migraines, eating disorders and obesity. Neural stimulation therapies can involve intermittent neural stimulation.

At the 2006 European Society of Cardiology meeting, De Ferrari et al. showed preliminary results from a study of chronic vagal nerve stimulation study in heart failure patients, where Class III heart failure patients were provided six months of therapy, uncontrolled, using an implantable vagal stimulator designed to reduce heart rate. The stimulator delivered selective efferent stimulation to the vagus nerve, targeted to slow the heart rate, and used sensed heart rate as a negative feedback therapy control that delivers vagus nerve stimulation when the heart rate is elevated and shuts off vagus nerve stimulation when the heart rate falls below a threshold. The stimulator continuously delivered vagus nerve stimulation when the heart rate is elevated, and synchronized the vagus nerve stimulation with the heart rate. The data indicated improvement over the first three months with regression over the next three months. De Ferrari et al. hypothesized that the regression was due to the severity and unstoppable progression of the underlying disease.

SUMMARY

In addition or alternative to the hypothesis that the regression is due to the progression of the underlying disease in human studies, another possible explanation or contributing factor for the regression observed in the preliminary results is physiological habituation to the vagus nerve stimulation therapy delivered in the study. The present subject matter is based on a developed neural stimulator prototype used in multiple animal studies that does not exhibit the regression illustrated in the presented results of the De Ferrari et al. study.

An embodiment relates to a method for delivering a vagal stimulation therapy to a vagus nerve, including delivering a neural stimulation signal to non-selectively stimulate both afferent axons and efferent axons in the vagus nerve according to a predetermined schedule for the vagal stimulation therapy, and selecting a value for at least one parameter for the predetermined schedule for the vagal stimulation therapy to control the neural stimulation therapy to avoid physiological habituation to the vagal stimulation therapy. The parameter(s) include at least one parameter selected from the group of parameters consisting of a predetermined therapy duration parameter for a predetermined therapy period, and a predetermined intermittent neural stimulation parameter associated with on/off timing for the intermittent neural stimulation parameter.

An embodiment relates to a method including, using an external device to program at least one neural stimulation schedule parameter for controlling a scheduled neural stimulation therapy of an implantable neural stimulator, and delivering the scheduled neural stimulation therapy using the implantable neural stimulator, including delivering non-selective neural stimulation to both afferent and efferent axons of a vagus nerve. The neural stimulation schedule parameter(s) includes at least one parameter with a value selected to control the neural stimulation therapy to avoid physiological habituation to the vagal stimulation therapy. The neural stimulation schedule parameter(s) includes at least one parameter selected from the group of parameters consisting of at least one predetermined therapy duration parameter for a predetermined therapy period, and at least one predetermined intermittent neural stimulation parameter associated with on/off timing for the intermittent neural stimulation parameter.

A neural stimulator embodiment includes a neural stimulation delivery system and a controller operationally connected to the neural stimulation delivery system. The neural stimulation delivery system is adapted to non-selectively stimulate both afferent axons and efferent axons in a vagus nerve. The controller includes a neural stimulation scheduler to control neural stimulation from the neural stimulation system according to a predetermined schedule. The predetermined schedule includes at least one parameter with a value selected to avoid physiological habituation to the neural stimulation. The parameter(s) include at least one parameter selected from the group of parameters consisting of a predetermined therapy duration parameter for a predetermined therapy period, and a predetermined intermittent neural stimulation parameter associated with on/off timing for the intermittent neural stimulation parameter.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
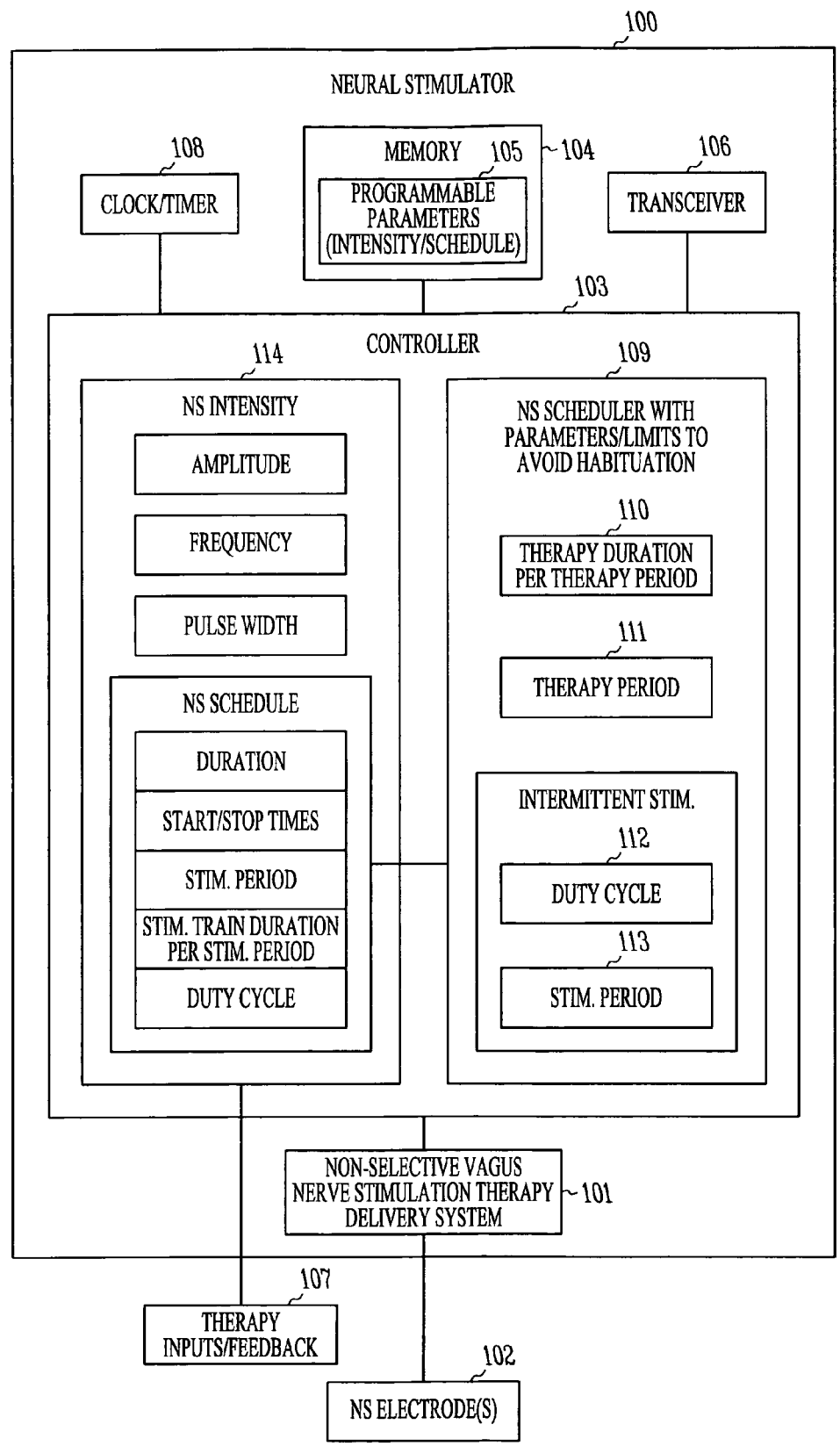
FIG. 1 illustrates a neural stimulator device embodiment. The illustrated device 100 is adapted to deliver chronic neural stimulation.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

An embodiment of the present subject matter provides vagus nerve stimulation for heart failure therapy, where the vagus nerve stimulation therapy avoids or prevents habituation to the therapy and maintains the efficacy of the vagus nerve stimulation therapy. According to various embodiments, the heart failure therapy (or other vagus nerve stimulation therapy) of the present subject matter provides non-selective stimulation of the vagus nerve, such that both efferent and afferent vagal axons are stimulated, and delivers the stimulation according to a stimulation schedule independent of the sensed heart rate. The afferent stimulation may be important in avoiding the habituation effect. Stimulation of the afferent axons in the vagus nerve stimulates a baroreflex. The naturally occurring baroreflex mechanism involves a neural pathway from an afferent neural pathway to the central nervous system through an efferent neural pathway to nerves that control dilation/constriction of the blood vessel. Sensory nerve endings that are sensitive to pressure, referred to as baroreceptors, function as a receptor for the baroreflex mechanism. If the central nervous system senses an increase in blood pressure from sensory nerve endings sensitive to pressure through an afferent pathway, the central nervous system controls nerves to, among other things, dilate blood vessels to reduce pressure.

It is believed that neural stimulation delivered on demand (during periods of elevated heart rate as delivered by the stimulator in the Farrari et al. study) will be primarily delivered while the patient is awake, as the patient likely has lowered heart rate during sleep. As heart failure reverses with the delivery of therapy, the heart rate will slow. It is believed that a heart failure therapy involving on-demand, selective efferent vagus nerve stimulation targeted to slow heart rate does not avoid physiological habituation to the efferent stimulation of the vagus nerve. Further, the negative feedback control based on sensed heart rate for the efferent vagus nerve stimulation causes the heart failure therapy to be withdrawn (the duration of stimulation over a period of time becomes less) as the heart failure reverses with the delivery of therapy. Rather, some embodiments of the present subject matter chronically deliver intermittent or continuous stimulation according to a schedule that delivers the vagus nerve stimulation for at least a minimum time per day. For example, intermittent stimulation, even at the same 24-hour average duty cycle, would be designed to be delivered for at least a specified number of hours per day.

It is believed that prolonged neural stimulation, such as a duty cycle over 50%, may result in physiological adaptation to the stimulation. Some embodiments of the present subject matter limit the duty cycle of continuous neural stimulation delivered during a scheduled neural stimulation session. For example, an embodiment limits the duty cycle to below 50%. Some embodiments limit the stimulation period for the intermittent stimulation cycle. For example, some embodiments limit the stimulation period to a time under five minutes, such that a new neural stimulation train will begin within five minutes of the previous neural stimulation train. Some embodiments, for example, deliver neural stimulation on the order of ten seconds per minute (duty cycle≈17%; neural stimulation period≈1 minute; duration of neural stimulation train≈ten seconds).

Provided below, for the benefit of the reader, is a brief discussion of physiology and therapies. The disclosure continues with a discussion of various device, system and method embodiments.

Physiology

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force is increased when the sympathetic nervous system is stimulated, and is decreased when the sympathetic nervous system is inhibited (the parasympathetic nervous system is stimulated). An afferent nerve conveys impulses toward a nerve center. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intention, increases urine secretion, and contracts the wall and relaxes the sphincter of the bladder. The functions associated with the sympathetic and parasympathetic nervous systems are many and can be complexly integrated with each other.

Vagal modulation may be used to treat a variety of cardiovascular disorders, including heart failure, post-MI remodeling, and hypertension. These conditions are briefly described below.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Therapies

The present subject matter relates to systems, devices and methods for providing neural stimulation, such as vagus nerve stimulation, and further relates to delivering neural stimulation therapy (NST) with parameter(s) selected to avoid habituation. Various embodiments provide a stand-alone device, either externally or internally, to provide neural stimulation therapy. The present subject matter can be implemented in cardiac applications for neural stimulation or in non-cardiac applications for neural stimulation where a diverse nerve (such as the vagus nerve) is stimulated. For example, the present subject matter may deliver anti-remodeling therapy through neural stimulation as part of a post-MI or heart failure therapy. The present subject matter may also be implemented in non-cardiac applications, such as in therapies to treat epilepsy, depression, pain, obesity, hypertension, sleep disorders, and neuropsychiatric disorders. Various embodiments provide systems or devices that integrate neural stimulation with one or more other therapies, such as bradycardia pacing, anti-tachycardia therapy, remodeling therapy, and the like.

Neural Stimulation Therapies

Examples of neural stimulation therapies include neural stimulation therapies for respiratory problems such a sleep disordered breathing, for blood pressure control such as to treat hypertension, for cardiac rhythm management, for myocardial infarction and ischemia, for heart failure, for epilepsy, for depression, for pain, for migraines and for eating disorders and obesity. Many proposed neural stimulation therapies include stimulation of the vagus nerve. This listing of other neural stimulation therapies is not intended to be an exhaustive listing. Neural stimulation can be provided using electrical, acoustic, ultrasound, light, and magnetic therapies. Electrical neural stimulation can be delivered using any of a nerve cuff, intravascularly-fed lead, or transcutaneous electrodes.

A therapy embodiment involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy or ART. When delivered in conjunction with ventricular resynchronization pacing, also referred to as remodeling control therapy (RCT), such modulation of autonomic activity may act synergistically to reverse or prevent cardiac remodeling.

One neural stimulation therapy embodiment involves treating hypertension by stimulating the baroreflex for sustained periods of time sufficient to reduce hypertension. The baroreflex is a reflex that can be triggered by stimulation of a baroreceptor or an afferent nerve trunk. Baroreflex neural targets include any sensor of pressure changes (e.g. sensory nerve endings that function as a baroreceptor) that is sensitive to stretching of the wall resulting from increased pressure from within, and that functions as the receptor of the central reflex mechanism that tends to reduce that pressure. Baroreflex neural targets also include neural pathways extending from the baroreceptors. Examples of nerve trunks that can serve as baroreflex neural targets include the vagus, aortic and carotid nerves.

Myocardial Stimulation Therapies

Various neural stimulation therapies can be integrated with various myocardial stimulation therapies. The integration of therapies may have a synergistic effect. Therapies can be synchronized with each other, and sensed data can be shared between the therapies. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modem ICDs typically have ATP capability, and deliver ATP therapy or a shock pulse when a tachyarrhythmia is detected.

Devices/Systems/Methods

FIG. 1 illustrates a neural stimulator device embodiment. The illustrated device 100 is adapted to deliver chronic neural stimulation. The device can be designed as an implantable device or an external device. A device embodiment includes an implantable device that provides chronic vagus nerve stimulation. The illustrated device includes a non-selective vagus nerve stimulation therapy delivery system 101 adapted to deliver a neural stimulation signal to the neural stimulation electrode(s) or transducer(s) 102 to deliver the neural stimulation therapy. Examples of neural stimulation electrodes include nerve cuff electrodes, intravascularly placed electrodes, and transcutaneous electrodes. Examples of neural stimulation transducers includes ultrasound, light and magnetic energy transducers. A controller 103 appropriately controls the neural stimulation therapy delivery system 101 to provide the appropriate neural stimulation signal to the electrode(s)/transducer(s) that results in a desired neural stimulation therapy. The illustrated device includes a memory 104 to store programmable parameters 105. The controller 103 implements a neural stimulation therapy using the programmable parameters. Examples of programmable parameters 105, any one or more of which can be stored in the memory, include a therapy duration parameter, a therapy period, as well as a duty cycle, and a stimulation therapy for intermittent stimulation. The programmable parameters can also include parameters used to adjust the intensity of the neural stimulation therapy, such as amplitude, frequency, pulse width, and stimulation schedule parameters. The illustrated device 100 includes a transceiver 106 adapted to communicate with an external device (e.g. programmer) for use in receiving programming instructions. The illustrated device 100 includes at least one port 107 for receiving neural stimulation therapy inputs or neural stimulation feedback inputs (including both therapy and feedback inputs according to some embodiments). The input can receive a communication from a device programmer, for use by a physician or patient in changing the programmable parameters based on observed conditions. The input can receive a feedback from physiologic sensors used to monitor physiologic responses to the neural stimulation. Examples of such sensors used to provide feedback for the transition protocol include heart rate and blood pressure sensors.

The illustrated device 100 includes a clock/timer 108, used by the controller 103 to control timing of the neural stimulation signals for the neural stimulation therapy. The illustrated controller 103 includes a neural stimulation scheduler 109, which uses the clock/timer and schedule parameter(s) to control the stimulation delivered by the delivery system 101. The scheduler uses at least one schedule parameter selected to avoid physiological habituation to the neural stimulation therapy. Some scheduler embodiments use a duration parameter(s) 110 to control the therapy duration per therapy period, and some scheduler embodiments use a therapy period parameter 111 to control a duration of time before a subsequent therapy is applied. For example, some embodiments use a therapy period of approximately one day, and use a therapy duration of approximately 8 hours each day. These parameter(s) can represent limits (e.g. maximum, minimum, range) for the parameter values. Some embodiments, for example, use the therapy duration parameter as a minimum value, such that at least that duration of the therapy will be applied per therapy period (e.g. at least 8 hours of therapy per day). The delivered therapy can be intermittent or continuous. Some scheduler embodiments use parameter(s) to control intermittent stimulation during the therapy period, such as duty cycle 112 or stimulation period 113. The duty cycle represents the percentage of time during which stimulation is delivered for a stimulation period. A therapy period (e.g. on the order of a day) can include many stimulation periods (e.g. less than five minutes or on the order of one minute). Some embodiments limit the duty cycle to less than approximately 50%, some embodiments limit the duty cycle to less than approximately 25%, and some embodiments limit the duty cycle to a range between 10% and 20%. A scheduler embodiment implements a protocol where neural stimulation is delivered for approximately ten seconds every minute (e.g. duty cycle of approximately 17% and a stimulation period of approximately one minute). The scheduler parameters can include start and stop parameters, start and duration parameters, or other parameters that can be used to control the schedule of neural stimulation. Some of the parameter examples can be derived from others (e.g. start and stop times can be derived from start and duration). Some embodiments of the scheduler program or limit the stimulation period, where a train of neural stimulation pulses occurs with each stimulation period. For example, some embodiments limit or program the stimulation period to a value less than five minutes, and some embodiments limit or program the stimulation period to a value on the order of one minute (e.g. 50 seconds).

The illustrated controller 103 also includes a module to control neural stimulation intensity 114. Therapy inputs and/or therapy feedback 107 can be used to appropriately adjust one or more stimulation parameter(s) to increase, decrease or maintain a desired neural stimulation intensity. For example, the amplitude, frequency, and/or pulse width of a neural stimulation pulse train can be adjusted to titrate the neural stimulation intensity. Some embodiments adjust the neural stimulation schedule to adjust the neural stimulation intensity. Examples of schedule parameters include therapy duration, start/stop times, stimulation period, stimulation train duration per stimulation period, and duty cycle. For embodiments that allow some schedule parameters to be modified, as illustrated by the line between the neural stimulation schedule in the neural stimulation intensity module 114 and the neural stimulation scheduler 109, the scheduler limits the extent of any allowed modifications to the schedule parameters. For example, the duty cycle of the stimulation can be adjusted to a value less than or equal to the maximum duty cycle (e.g. 50%) permitted by the scheduler or within a range of duty cycles permitted by the scheduler. In another example, the therapy duration can be adjusted to a value greater than or equal to the minimum value (e.g. 8 hours per day) for the duration of the therapy permitted by the controller.

Advanced patient management systems can be used to enable the patient and/or doctor to adjust parameter(s) to avoid observed or sensed habituation, or to adjust therapy intensity. The inputs can be provided by computers, programmers, cell phones, personal digital assistants, and the like. The patient can call a call center using a regular telephone, a mobile phone, or the internet. The communication can be through a repeater, similar to that used in Boston Scientific's Latitude patient management system. In response, the call center (e.g. server in call center) can automatically send information to the device to adjust or titrate the therapy. The call center can inform the patient's physician of the event. A device interrogation can be automatically triggered. The results of the device interrogation can be used to determine if and how the therapy should be adjusted and/or titrated to improve the transient response. A server can automatically adjust and/or titrate the therapy using the results of the device interrogation. Medical staff can review the results of the device interrogation, and program the device through the remote server to provide the desired therapy adjustments and/or titrations. The server can communicate results of the device interrogation to the patient's physician, who can provide input or direction for adjusting and/or titrating the therapy.

Figure 2:
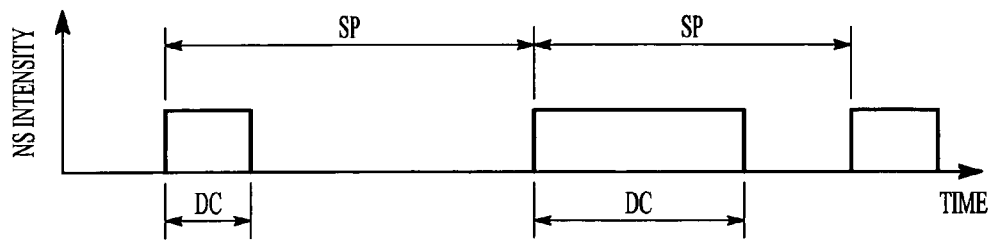
FIG. 2 illustrates an example of variable stimulation periods (SP) and duty cycles (DC).
Figure 3:
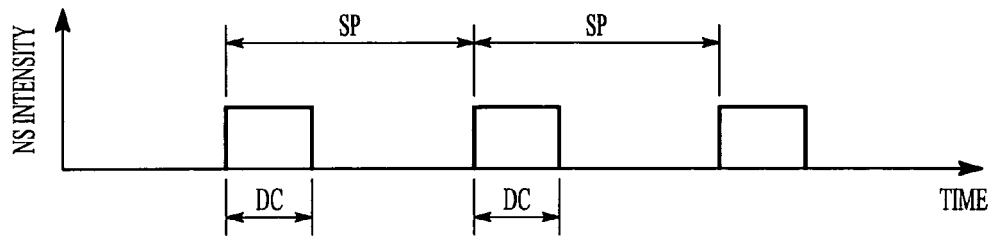
FIG. 3 illustrates an example of constant stimulation periods (SP) and duty cycles (DC).

Various embodiments of the present subject matter relate to neural stimulation therapy (NST) that includes intermittent neural stimulation. Some of the terms used to discuss intermittent stimulation are illustrated in FIGS. 2 and 3. Intermittent neural stimulation can be delivered using a duty cycle of a stimulation period. FIGS. 2 and 3 plot neural stimulation intensity against time. FIG. 2 illustrates variable stimulation periods (SP) and duty cycles (DC), and FIG. 3 illustrates constant stimulation periods (SP) and duty cycles (DC). Each duty cycle can include a train of neural stimulation pulses. The duty cycle and stimulation period need not be constant throughout the NST. For example, the duration or frequency of the duty cycle can be adjusted to adjust an intensity of the NST. Also, the start and/or stop of the duty cycle can be dependent on enabling conditions. The duty cycle and/or stimulation period can be adjusted in every subsequent stimulation period. Unless expressly disclosed otherwise herein, "stimulation period" and "duty cycle" are not intended to only encompass constant values that result in neural stimulation in a precise periodic manner (e.g. FIG. 3), but rather is intended to include intermittent neural stimulation where therapeutically-effective or prophylactically-effective neural stimulation is delivered for a time and then not delivered for a time, and then delivered for a time (e.g. FIG. 2).

The neural stimulation delivered during the duty cycle can be delivered using a variety of neural stimulation techniques, such as stimulation that uses electrical, ultrasound, thermal, magnetic, light or mechanical energy. Electrical neural stimulation is used in this document as an example of neural stimulation. In electrical stimulation, for example, a train of neural stimulation pulses (current or voltage) can be delivered during a duty cycle of stimulation. Stimulation waveforms can be square pulses or other morphologies. The stimulation pulses can be monophasic or biphasic pulses.

In addition to controlling the schedule of the neural stimulation to avoid physiological habituation to the stimulation, some embodiments also implement a protocol designed to mimic the effects of the naturally-occurring pulse pressure, as provided in U.S. application Ser. No. 10/962,845, filed Oct. 12, 2004 (U.S. Published Application 2006/0079945). As discussed therein, the baroreflex adapts to increased baroreflex stimulation. Static or constant baroreflex stimulation causes a quick or immediate response which gradually diminishes. Over time, the baroreflex resets and returns to the baseline response, which renders static stimulation ineffective. Thus, baroreflex adaptation poses a problem for sustaining baroreflex therapy that effectively inhibits SNA.

Figure 4:
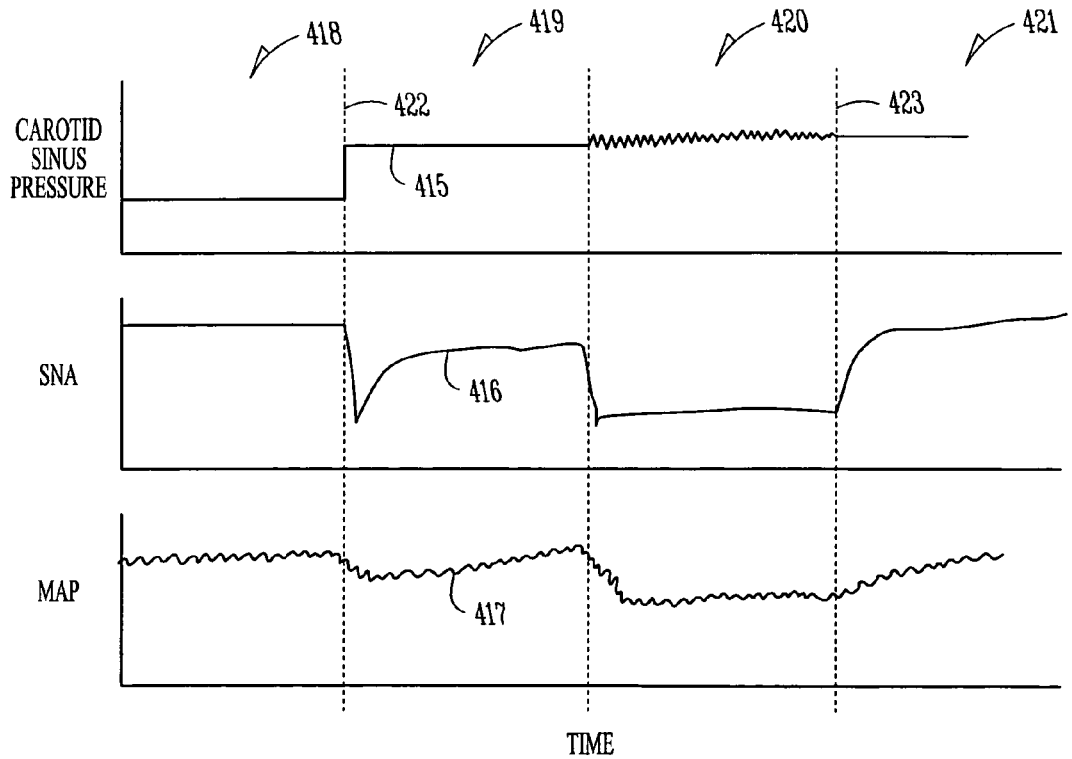
FIG. 4 illustrates baroreflex adaptation using a relationship between carotid sinus pressure, sympathetic nerve activity (SNA) and mean arterial pressure (MAP).

FIG. 4 illustrates baroreflex adaptation using a relationship between carotid sinus pressure 415, sympathetic nerve activity (SNA) 416 and mean arterial pressure (MAP) 417. Internal pressure and stretching of the arterial wall, such as that which occurs at the carotid sinus, naturally activates the baroreflex and the baroreflex inhibits SNA. The carotid sinus pressure, the SNA and the MAP are illustrated for the following four time segments: (1) relatively low and constant carotid sinus pressure indicated at 418; (2) relatively high and constant carotid sinus pressure indicated at 419; (3) relatively high and pulsed carotid sinus pressure indicated at 420; and (4) a return to a relatively high and constant carotid sinus pressure indicated at 421.

When the carotid sinus pressure is relatively low and constant, as illustrated at 418, the SNA is relatively high and constant, and the pulsating MAP is relatively high. When the carotid sinus pressure is increased to a relatively high and constant pressure at transition 422, the SNA and MAP initially decrease due to the baroreflex and then increases due to the quick adaptation of the baroreflex to the increased carotid sinus pressure. However, when the carotid sinus pressure pulsates similar to naturally-occurring blood pressure pulses, as illustrated at 420, the SNA and MAP decrease to relatively low levels and are maintained at these relatively low levels. When the carotid sinus pressure changes from a pulsed to constant pressure at transition 423, the SNA and MAP both increase again due to the adaptation of the baroreflex. Some embodiments modulate the baroreflex stimulation to mimic the effects of the naturally-occurring pulse pressure and prevent baroreflex adaptation.

Figure 5:
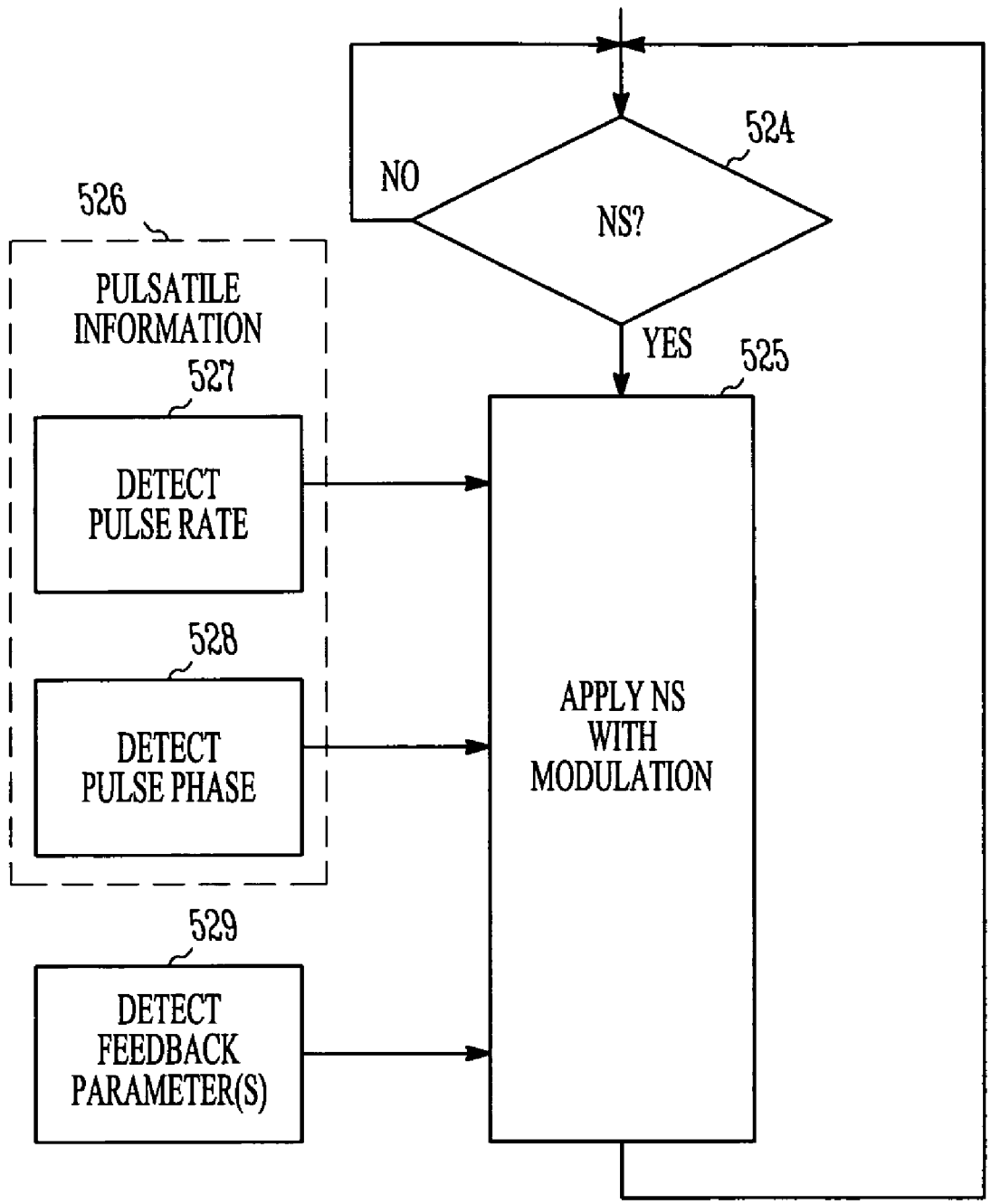
FIG. 5 illustrates a method to periodically modulate neural stimulation, according to various embodiments of the present subject matter.

FIG. 5 illustrates a method to periodically modulate neural stimulation, according to various embodiments of the present subject matter. At 524, it is determined whether neural stimulation is to be provided. Upon determining that neural stimulation is to be provided, neural stimulation is applied with periodic modulation to mimic pulsatile pressure, as generally illustrated at 525. In various embodiments, the periodic modulation, or other variation, of the neural stimulation signal is based on detected pulsatile information 526 such as a detected pulse rate 527 and/or a detected pulse phase 528. Some embodiments further base the periodic modulation based on detected feedback parameters 529, such as detected respiration, detected nerve traffic, detected blood pressure, and the like. These feedback parameters allow the stimulation to be tailored to achieve a desired effect.

An embodiment of the neural stimulation therapy delivery system 101 illustrated in FIG. 1 uses neural stimulation waveforms disclosed in U.S. application Ser. No. 11/468,135, filed Aug. 29, 2006. According to an embodiment, the stimulation circuitry is configured to deliver a waveform for neural stimulation with the following approximate parameters: frequency=20 Hz; pulse width=300 microseconds; amplitude=1.5-2.0 mA. This waveform can be delivered as a pulse train applied either continuously or intermittently (e.g., with a duty cycle=10 sec ON, 50 sec OFF) in order to provide, for example, anti-remodeling therapy to post-MI or heart failure patients. Such stimulation may be applied either chronically or periodically in accordance with lapsed time intervals or sensed physiological conditions. This waveform has been demonstrated in pre-clinical studies to be a particularly effective anti-remodeling therapy when applied to the vagus nerve in the cervical region, where the stimulation may be applied through either a nerve cuff or a transvascular lead. The stimulating configuration for delivering the waveform may be any of the configurations described in this document such as either a bipolar configuration or a unipolar configuration with a far-field subcutaneous return electrode. The stimulation circuitry may be either dedicated to delivering neural stimulation or may be configured to also deliver waveforms suitable for CRM.

Figure 6:
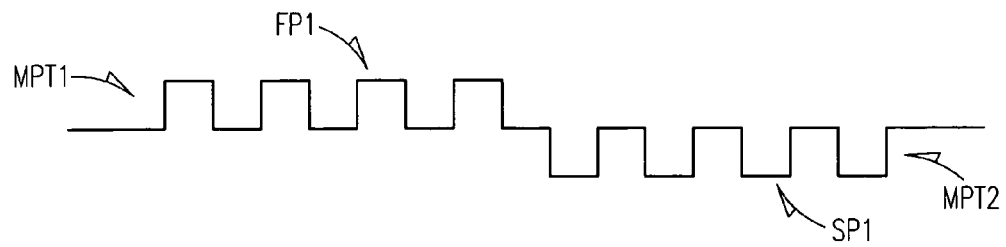
FIGS. 6 and 7 show example waveforms as would be produced by recording the potential between stimulation electrodes.
Figure 7:
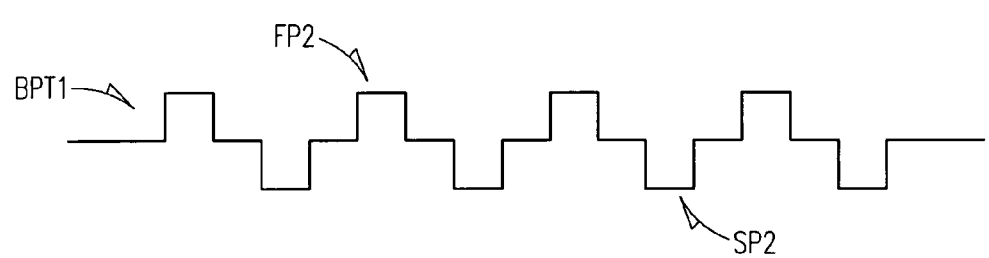

A neural stimulation waveform may be delivered with phases of alternating polarity, referred to herein as first and second phases. For example, the waveform may be delivered as monophasic pulses with a bipolar stimulating configuration and with a "bipolar switch" so that the phase of the monophasic pulses is alternated in each consecutive pulse train. That is, a pulse train with monophasic pulses having first phases of one polarity is then followed by a pulse train with monophasic pulses having second phases of the opposite polarity. FIGS. 6 and 7 show example waveforms as would be produced by recording the potential between the stimulation electrodes. FIG. 6 shows an example of such a waveform in which a monophasic pulse train MPT1 having first phases FP1 of positive polarity is followed by a monophasic pulse train MPT2 having second phases SP1 of negative polarity. In another embodiment, the stimulation circuitry may be configured to deliver a pulse train with biphasic pulses so that the first phase alternates with the second phase (i.e., each consecutive pulse in the train alternates in polarity). FIG. 7 shows an example of a biphasic pulse train BPT1 having first phases FP2 and second phases SP2 that alternate in polarity. Such biphasic pulse trains with alternating polarities or a series of monophasic pulses trains having alternating polarities may be applied continuously or on a periodic or intermittent basis for a specified period of time.

Figure 8:
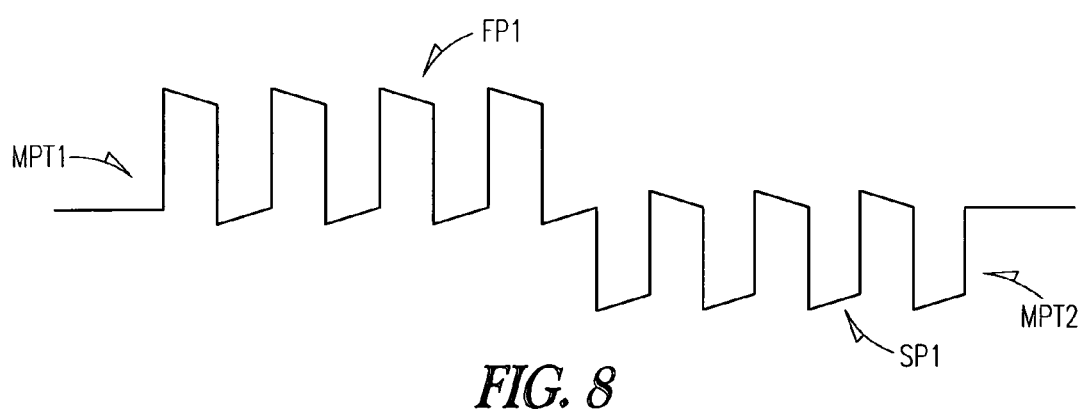
FIGS. 8 and 9 show example waveforms as would be produced by a capacitive discharge pulse output circuit.
Figure 9:
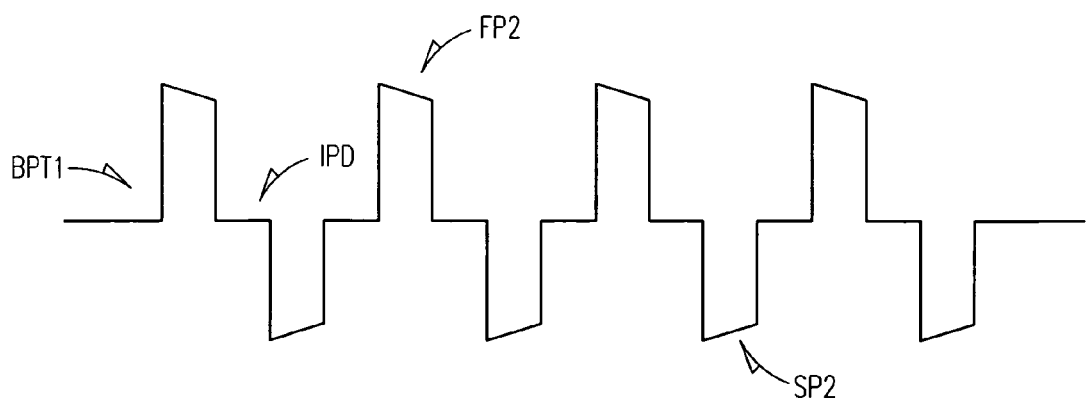

FIGS. 8 and 9 show example waveforms as would be produced by a capacitive discharge pulse output circuit, which correspond to the waveforms of FIGS. 6 and 7, respectively. With a capacitive discharge pulse output circuit, the voltage amplitude of each pulse is not constant as is the case with a current source pulse output circuit. FIGS. 8 and 9 thus show pulses in which the voltage rises to an initial value and then decays as the output capacitor discharges. Also, the circuitry may incorporate a passive recharge between monophasic pulses in order to dissipate afterpotentials from the stimulation electrodes. FIG. 8 shows such passive recharge cycles where the output circuitry is switched in a manner that causes the voltage between pulses overshoots slightly in a direction opposite to the pulses and decays to zero as the afterpotentials between the stimulation electrodes discharge. Passive recharge is not needed in the case of biphasic pulses as each pulse discharges the afterpotential produced by the preceding pulse. FIG. 9 shows an interphase delay IPD between biphasic pulses. In certain embodiments, it may be desirable to minimize or even eliminate this delay.

Figure 10:
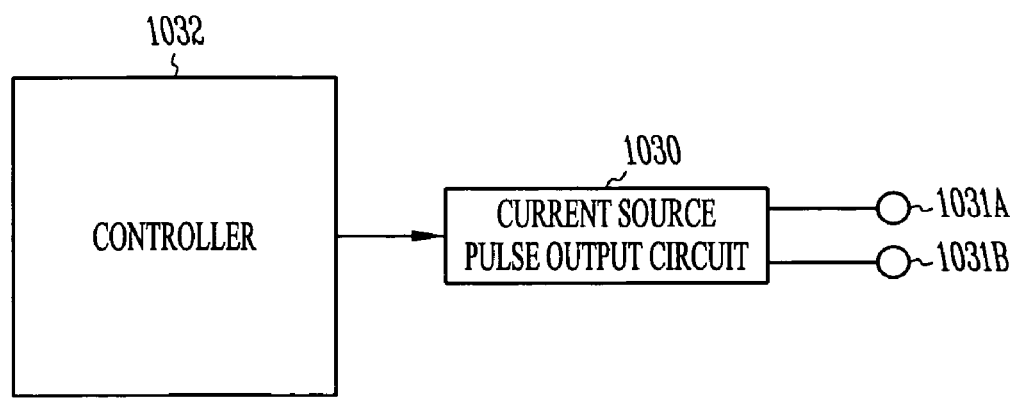
FIGS. 10 and 11 illustrate embodiments of circuitry for delivering stimulation pulse trains.
Figure 11:
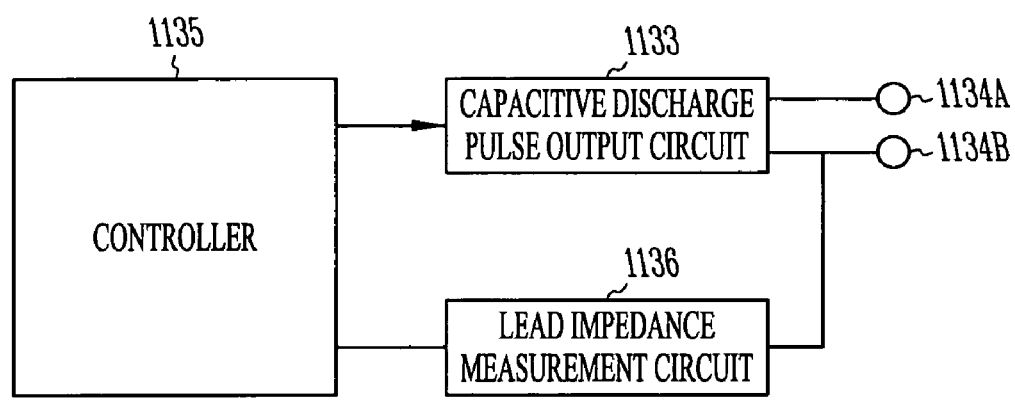

FIGS. 10 and 11 illustrate embodiments of circuitry for delivering stimulation pulse trains as described above. In FIG. 10, a current source pulse output circuit 1030 outputs current pulses between stimulation electrodes 1031A and 1031B in accordance with command inputs from the controller 1032. The command inputs from the controller specify the timing of the pulses, pulse widths, current amplitude, and polarity. FIG. 11 illustrates an embodiment in which a capacitive discharge pulse output circuit 1133 is used to output voltage pulses between stimulation electrodes 1134A and 1134B in accordance with command inputs from the controller 1135. In this embodiment, the command inputs from the controller specify the timing of the pulses, pulse widths, voltage amplitude, and pulse polarity. In order for the controller to specify a voltage amplitude that results in a desired current amplitude for the pulses, the lead impedance may be measured by lead impedance measurement circuit 1136. The output capacitor of the pulse output circuit may then be charged to the appropriate voltage for each pulse. In order to monitor the lead impedance, the controller is programmed to periodically, or upon command from a user via telemetry, charge the output capacitor to a known voltage level, connect the output capacitor to the stimulation leads to deliver a stimulation pulse, and measure the time it takes for the capacitor voltage to decay by a certain amount (e.g., to half of the initial value). In order to minimize patient discomfort, the lead impedance procedure should be performed using as low a voltage as possible. In one embodiment, the controller is programmed to use a first voltage amplitude (e.g., 1 volt) and then compare the measurement count (i.e., the capacitor decay time) to a specified minimum value CntZMin. If the measurement count is below CntZMin, the current delivered during the test is deemed too small for the measurement to be accurate. A second measurement pulse is then delivered at a higher second voltage (e.g., 2 volts). If that count is again below CntZMin, a third measurement pulse is delivered at a still higher third voltage (e.g., 4 volts). With a typical stimulation lead, this procedure limits the measurement current to between roughly 1 mA and 0.6 mA.

In an embodiment, with either a biphasic pulse train or a series of monophasic pulse trains having alternating polarities, the stimulation parameters for the first and second phases may be adjusted separately. For example, the pulse widths and amplitudes for the first and second phases of a biphasic pulse train may be selected to be the same or different. In the case of a series of monophasic pulse trains having alternating polarities, the pulse width, pulse amplitude, duty cycle, and frequency for each of the first and second phases may be selected to be the same or different.

In an embodiment, advantage is taken of an empirical finding that stimulation of the vagus nerve with pulses of different polarities can have different effects. It has been found that vagal stimulation with alternating polarities, delivered as either a biphasic pulse train or by monophasic pulse trains with alternating polarities, results not only in the desired therapeutic effect for preventing or reversing cardiac remodeling as described above, but also with a reduction of undesired side effects. Such side effects from vagal stimulation may include, for example, hoarseness and coughing due to vagal innervation of the larynx. In order to achieve an optimum balance between therapeutic effects and undesired side effects, a neural stimulation waveform with alternating polarities may be applied over time while varying the pulse amplitudes and pulse widths for each polarity. As the pulse amplitudes and widths are varied, a clinical determination may be made as to the therapeutic benefit provided and the extent of any undesired side effects. For example, a biphasic pulse train or a series monophasic pulse trains with alternating polarities may be applied in which the pulse amplitude and pulse width for one polarity are titrated to a therapeutic dose. The pulse amplitude and pulse width for the opposite polarity are then adjusted to control the presence of side-effects. Which one of the two polarities of the pulse train is responsible for producing therapeutic benefits and which polarity is responsible for reducing side effects may be determined empirically. Such a titration procedure may be performed by a clinician after implantation of the device, where the stimulation parameters such as pulse width and amplitude are adjusted via telemetry. The device could also be configured to automatically titrate the therapeutic dose to a target amplitude within a specified period of time. For example, such a titration could be performed rapidly during the first 1-2 weeks after an MI, which has been shown in pre-clinical studies to be the time where the greatest therapeutic benefit is achieved.

The pulse frequency, pulse width, pulse amplitude, pulse polarity, and bipolar/unipolar stimulation configuration can be programmable parameters, the optimal settings of which depend upon the stimulation site and type of stimulation electrode. The device may also be equipped with different sensing modalities for sensing physiological variables affected by neural stimulation. The device may then be programmed to use these variables in controlling the delivery of neural stimulation.

Figure 12:
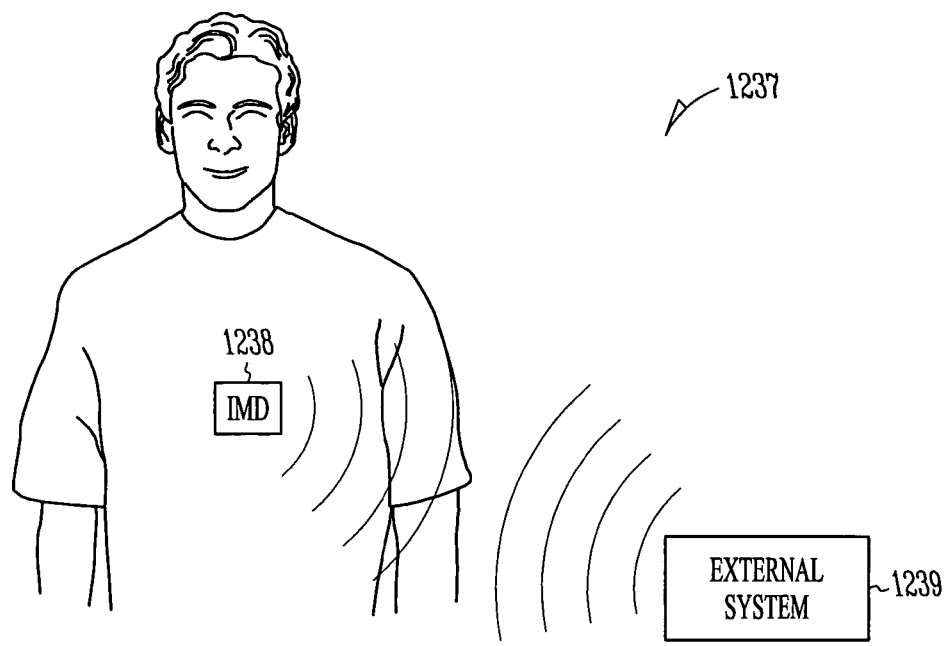
FIG. 12 illustrates a system including an implantable medical device (IMD) 1238 and an external system or device, according to various embodiments of the present subject matter.

FIG. 12 illustrates a system 1237 including an implantable medical device (IMD) 1238 and an external system or device 1239, according to various embodiments of the present subject matter. Various embodiments of the IMD include NS functions or include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates/inhibits a neural target using non-selective vagus nerve stimulation delivered using a predetermined schedule and with schedule parameter(s) selected to avoid physiological habituation to the vagus nerve stimulation.

The external system allows a user such as a physician or other caregiver or a patient to control the operation of the IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to IMD. This includes, for example, programming the IMD to acquire physiological data, programming IMD to perform at least one self-diagnostic test (such as for a device operational status), and programming the IMD to deliver at least one therapy.

Figure 13:
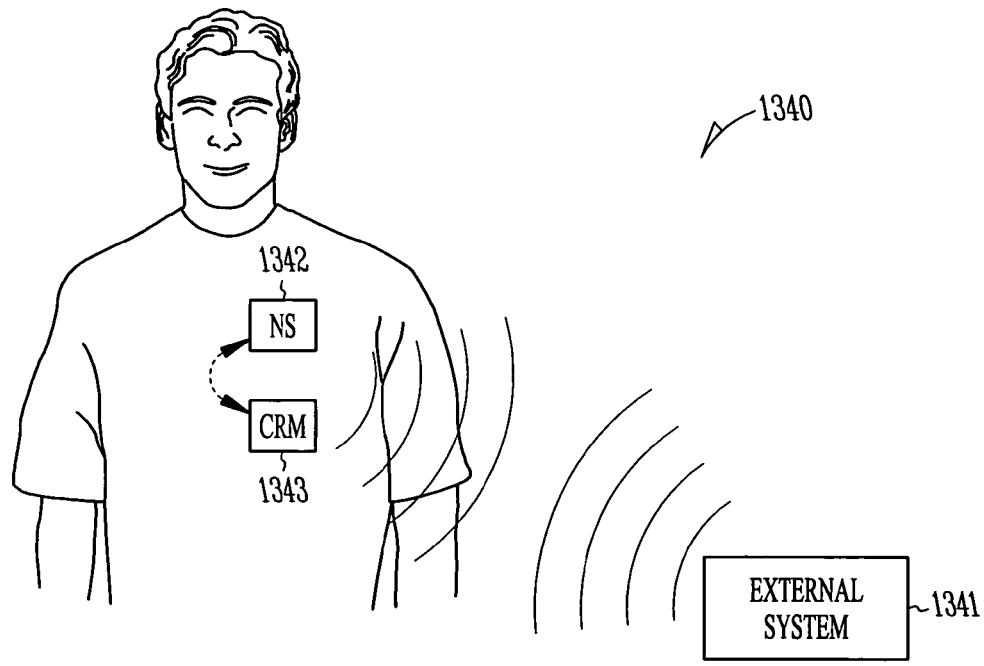
FIG. 13 illustrates a system including an external device, an implantable neural stimulator (NS) device and an implantable cardiac rhythm management (CRM) device, according to various embodiments of the present subject matter.

FIG. 13 illustrates a system 1340 including an external device 1341, an implantable neural stimulator (NS) device 1342 and an implantable cardiac rhythm management (CRM) device 1343, according to various embodiments of the present subject matter. Various aspects involve a method for communicating between an NS device and a CRM device or other cardiac stimulator. In various embodiments, this communication allows one of the devices 1342 or 1343 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

FIGS. 14-15 and 18-19 illustrate system embodiments adapted to provide vagal stimulation, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve.

Figure 14:
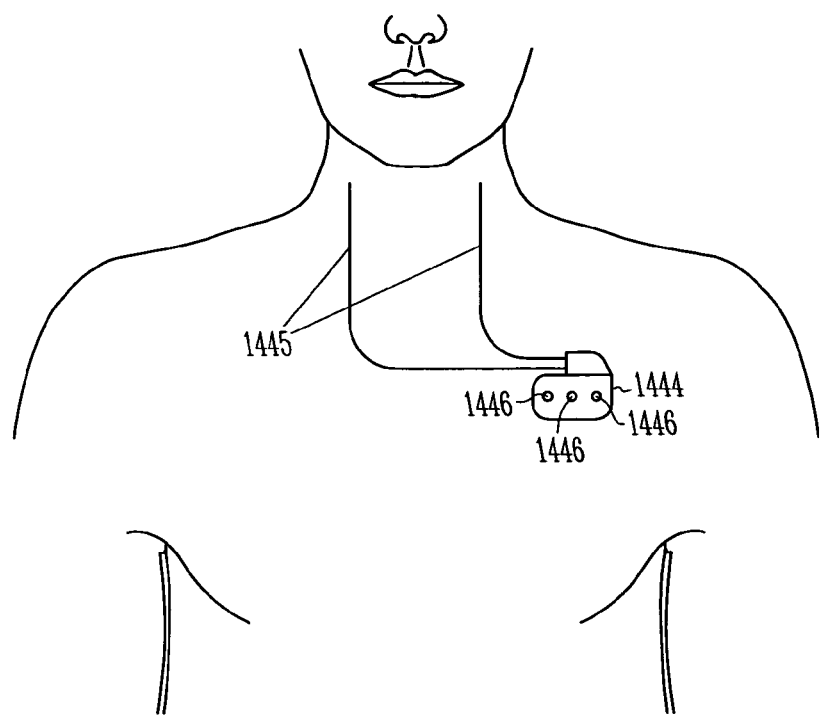
FIG. 14 illustrates a system embodiment in which an implantable medical device (IMD) is placed subcutaneously or submuscularly in a patient's chest with lead(s) positioned to stimulate a vagus nerve.

FIG. 14 illustrates a system embodiment in which an implantable medical device (IMD) 1444 is placed subcutaneously or submuscularly in a patient's chest with lead(s) 1445 positioned to stimulate a vagus nerve. According to various embodiments, neural stimulation lead(s) 1445 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subdlavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes 1446 on the housing of the device. These ECG electrodes are capable of being used to detect heart rate, for example. Heart rate can be used as a feedback to titrate the neural stimulation intensity. However, the neural stimulation is delivered based upon a predetermined schedule with schedule parameter(s) selected to avoid physiological habituation to the vagus nerve stimulation, and is not initiated on-demand based on the heart rate.

Figure 15:
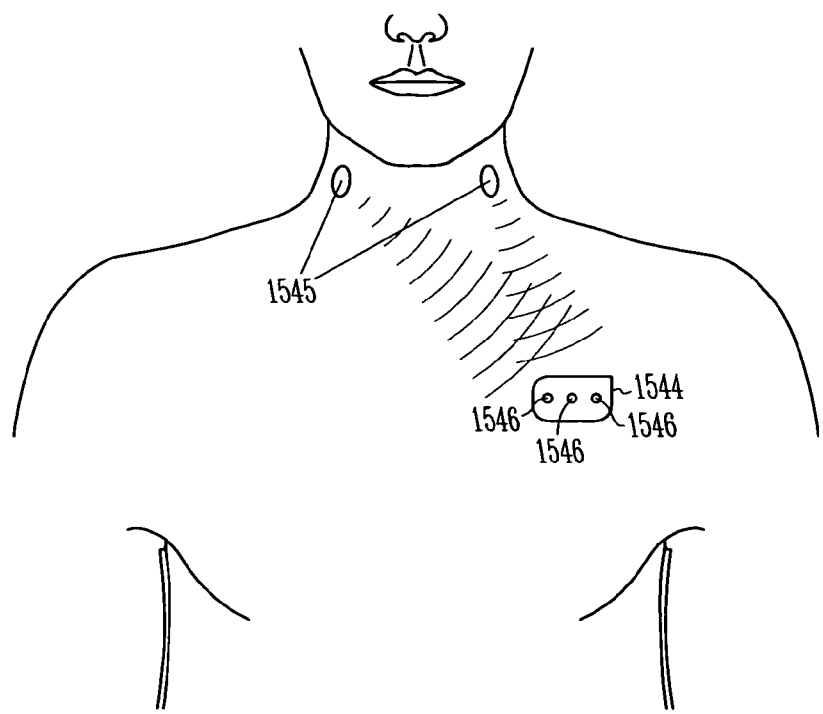
FIG. 15 illustrates a system embodiment that includes an implantable medical device (IMD) with satellite electrode(s) positioned to stimulate at least one neural target.

FIG. 15 illustrates a system embodiment that includes an implantable medical device (IMD) 1544 with satellite electrode(s) 1545 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes 1546 on the housing of the device. These ECG electrodes are capable of being used to detect heart rate, for example. Heart rate can be used as a feedback to titrate the neural stimulation intensity. However, the neural stimulation is delivered based upon a predetermined schedule with schedule parameter(s) selected to avoid physiological habituation to the vagus nerve stimulation, and is not initiated on-demand based on the heart rate.

Figure 16:
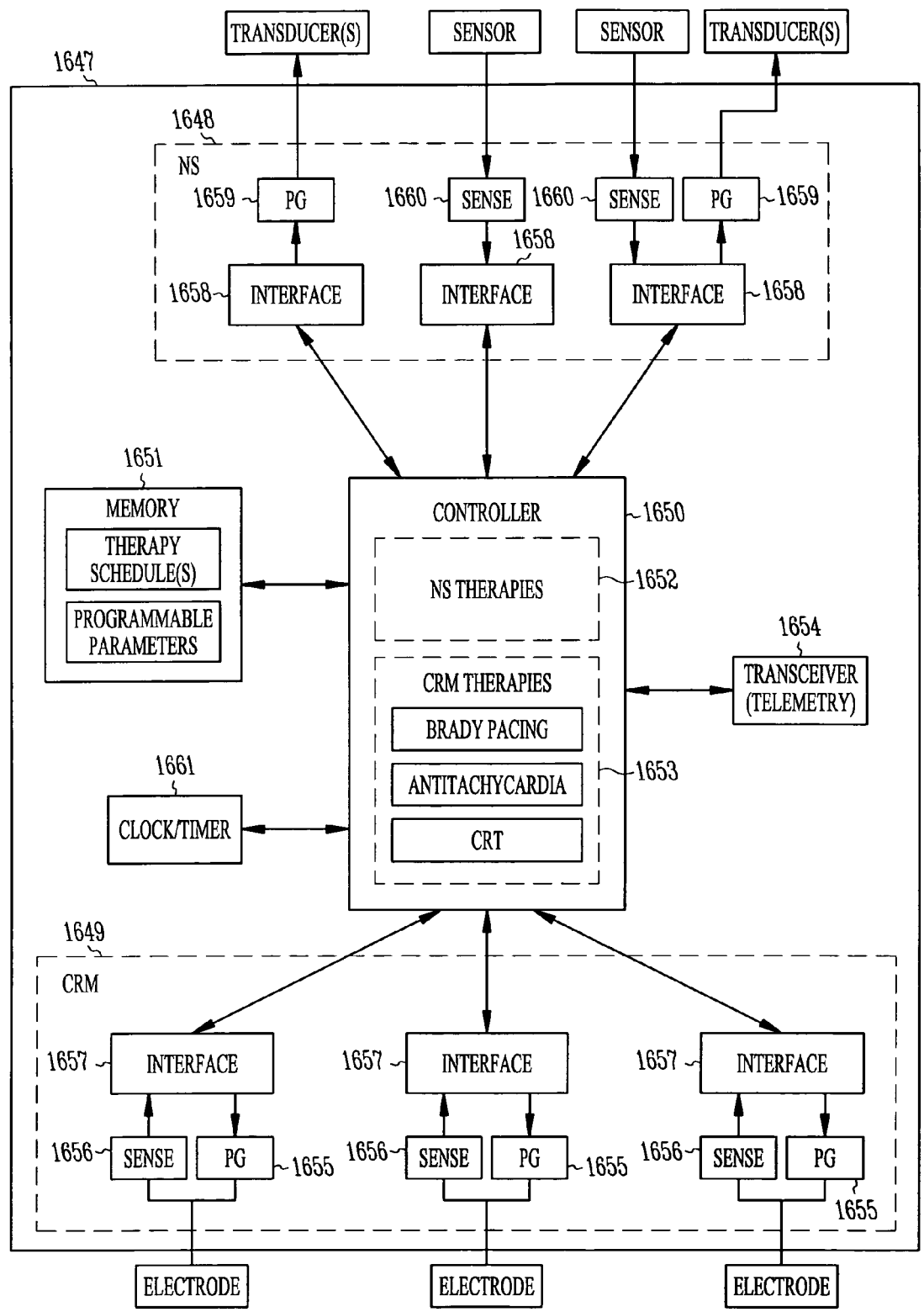
FIG. 16 illustrates an implantable medical device (IMD) having a neural stimulation (NS) component and a cardiac rhythm management (CRM) component according to various embodiments of the present subject matter.

FIG. 16 illustrates an implantable medical device (IMD) 1647 having a neural stimulation (NS) component 1648 and a cardiac rhythm management (CRM) component 1649 according to various embodiments of the present subject matter. The illustrated device includes a controller 1650 and memory 1651. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by one or more processors. For example, therapy schedule(s) and programmable parameters can be stored in memory. According to various embodiments, the controller includes a processor to execute instructions embedded in memory to perform the neural stimulation and CRM functions. The illustrated neural stimulation therapy 1652 can include any neural stimulation therapy, such as a vagus nerve stimulation therapy for heart failure. Various embodiments include CRM therapies 1653, such as bradycardia pacing, anti-tachycardia therapies such as ATP, defibrillation and cardioversion, and cardiac resynchronization therapy (CRT). The illustrated device further includes a transceiver 1654 and associated circuitry for use to communicate with a programmer or another external or internal device. Various embodiments include a telemetry coil.

The CRM therapy section 1649 includes components, under the control of the controller, to stimulate a heart and/or sense cardiac signals using one or more electrodes. The illustrated CRM therapy section includes a pulse generator 1655 for use to provide an electrical signal through an electrode to stimulate a heart, and further includes sense circuitry 1656 to detect and process sensed cardiac signals. An interface 1657 is generally illustrated for use to communicate between the controller 1650 and the pulse generator 1655 and sense circuitry 1656. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1648 includes components, under the control of the controller, to stimulate a neural stimulation target and/or sense parameters associated with nerve activity or surrogates of nerve activity such as blood pressure and respiration. Three interfaces 1658 are illustrated for use to provide neural stimulation. However, the present subject matter is not limited to a particular number interfaces, or to any particular stimulating or sensing functions. Pulse generators 1659 are used to provide electrical pulses to transducer or transducers for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 1660 are used to detect and process signals from a sensor, such as a sensor of nerve activity, blood pressure, respiration, and the like. The interfaces 1658 are generally illustrated for use to communicate between the controller 1650 and the pulse generator 1659 and sense circuitry 1660. Each interface, for example, may be used to control a separate lead. Various embodiments of the NS therapy section only includes a pulse generator to stimulate a neural target. The illustrated device further includes a clock/timer 1661, which can be used to deliver the programmed therapy according to a programmed stimulation protocol and/or schedule.

Figure 17:
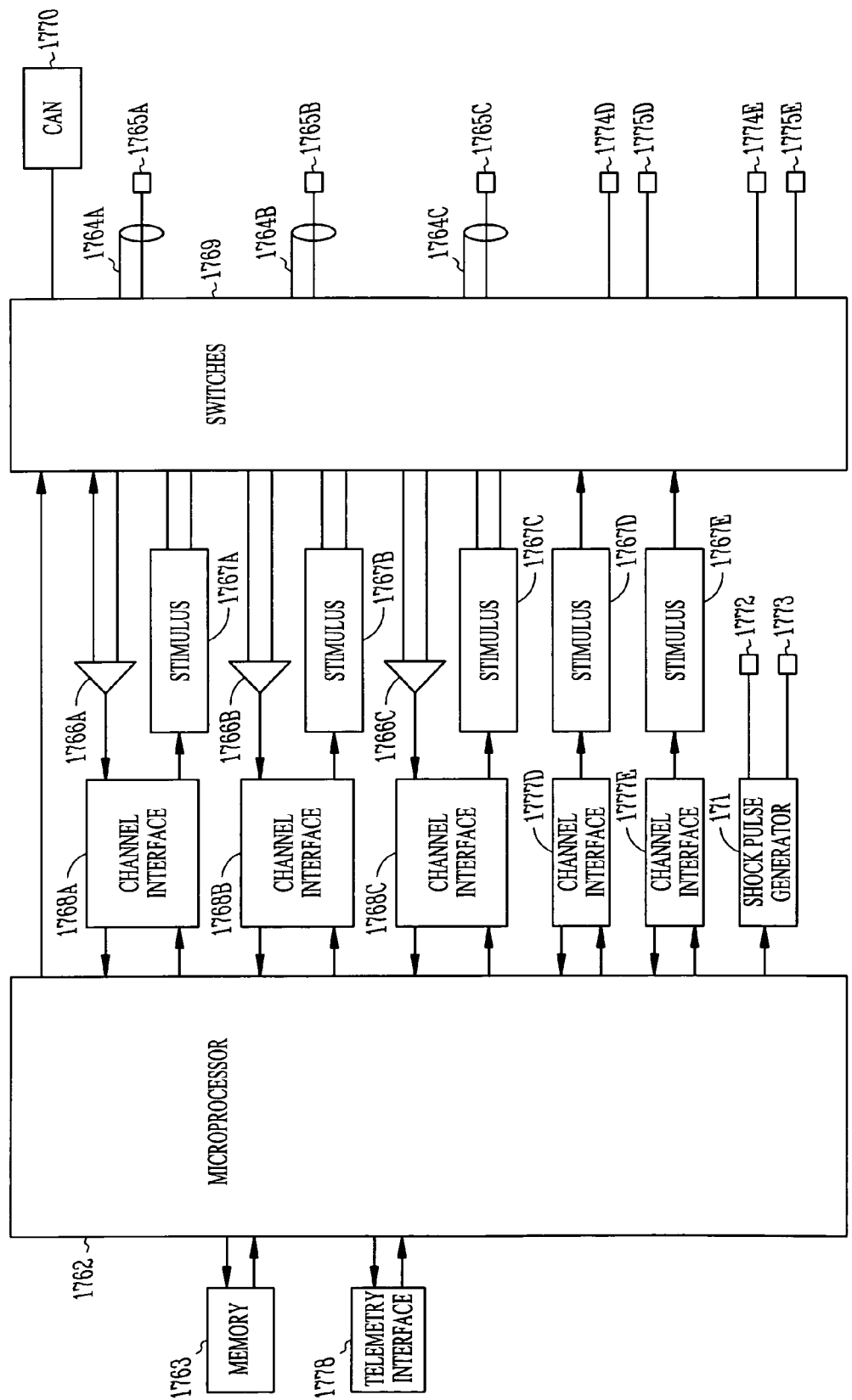
FIG. 17 shows a system diagram of an embodiment of a microprocessor-based implantable device, according to various embodiments.

FIG. 17 shows a system diagram of an embodiment of a microprocessor-based implantable device, according to various embodiments. The controller of the device is a microprocessor 1762 which communicates with a memory 1763 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1764A-C and tip electrodes 1765A-C, sensing amplifiers 1766A-C, pulse generators 1767A-C, and channel interfaces 1768A-C. Each channel thus includes a pacing channel made up of the pulse generator connected to the electrode and a sensing channel made up of the sense amplifier connected to the electrode. The channel interfaces 1768A-C communicate bidirectionally with the microprocessor 1762, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1769 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1770 or an electrode on another lead serving as a ground electrode. A shock pulse generator 1771 is also interfaced to the controller for delivering a defibrillation shock via shock electrodes 1772 and 1773 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1774D and a second electrode 1775D, a pulse generator 1776D, and a channel interface 1777D, and the other channel includes a bipolar lead with a first electrode 1774E and a second electrode 1775E, a pulse generator 1776E, and a channel interface 1777E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1778 connected to the microprocessor, which can be used to communicate with an external device. The illustrated microprocessor 1762 is capable of performing neural stimulation therapy routines and myocardial (CRM) stimulation routines. Examples of NS therapy routines include a vagus nerve stimulation therapies to treat ventricular remodeling, hypertension, and heart failure. The present subject matter is not limited to a particular neural stimulation therapy. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 18:
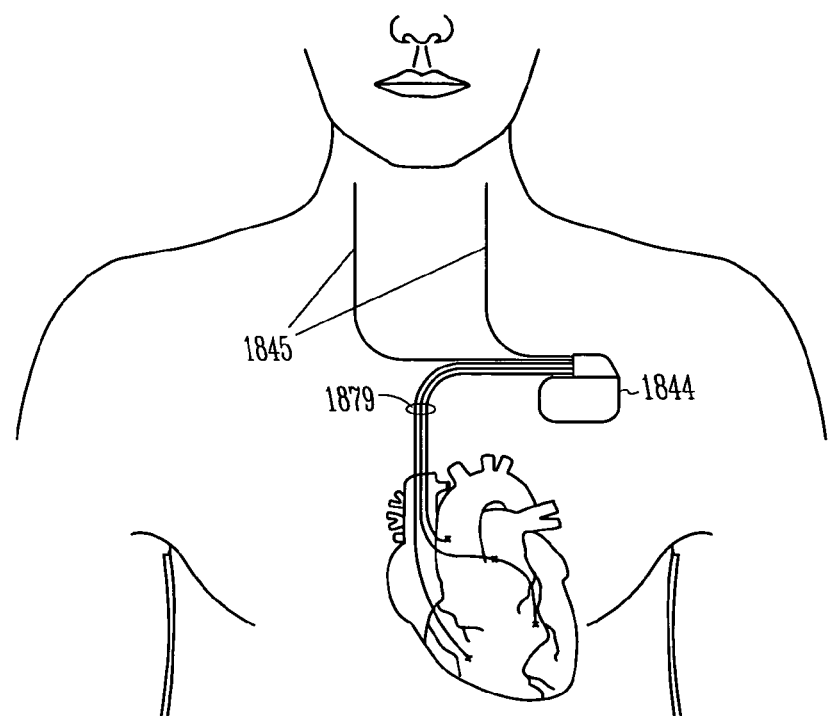
FIG. 18 illustrates an IMD placed subcutaneously or submuscularly in a patient's chest with lead(s) positioned to provide a CRM therapy to a heart, and with lead(s) positioned to stimulate and/or inhibit neural traffic at a neural target, such as a vagus nerve, according to various embodiments.

FIG. 18 illustrates an IMD 1844 placed subcutaneously or submuscularly in a patient's chest with lead(s) 1879 positioned to provide a CRM therapy to a heart, and with lead(s) 1845 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 19:
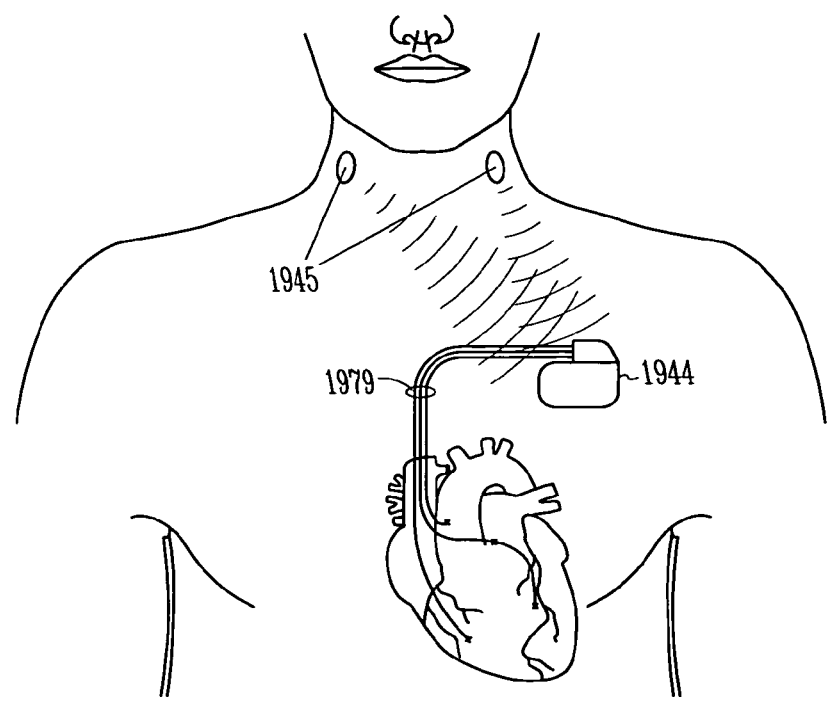
FIG. 19 illustrates an IMD with lead(s) positioned to provide a CRM therapy to a heart, and with satellite transducers positioned to stimulate/inhibit a neural target such as a vagus nerve, according to various embodiments.

FIG. 19 illustrates an IMD 1944 with lead(s) 1979 positioned to provide a CRM therapy to a heart, and with satellite transducers 1945 positioned to stimulate/inhibit a neural target such as a vagus nerve, according to various embodiments. The satellite transducers are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

Figure 20:
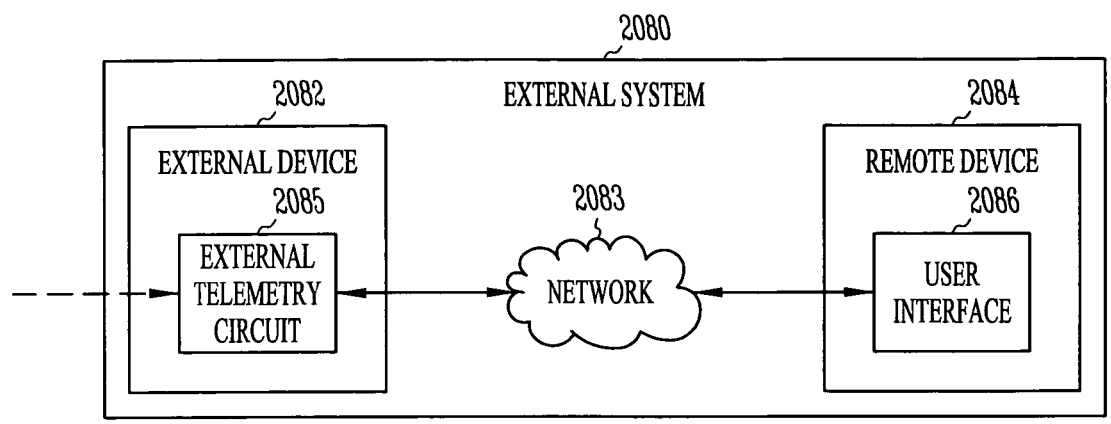
FIG. 20 is a block diagram illustrating an embodiment of an external system.

FIG. 20 is a block diagram illustrating an embodiment of an external system 2080. The external system includes a programmer, in some embodiments. In the illustrated embodiment, the external system includes a patient management system. As illustrated, the external system 2080 is a patient management system including an external device 2082, a telecommunication network 2083, and a remote device 2084. The external device 2080 is placed within the vicinity of an implantable medical device (IMD) and includes an external telemetry system 2085 to communicate with the IMD. The remote device(s) 2084 is in one or more remote locations and communicates with the external device 2082 through the network 2083, thus allowing a physician or other caregiver to monitor and treat a patient from a distant location and/or allowing access to various treatment resources from the one or more remote locations. The illustrated remote device 2084 includes a user interface 2086. According to various embodiments, the external device 2082 includes a neural stimulator, a programmer or other device such as a computer, a personal data assistant or phone. The external device 2082, in various embodiments, includes two devices adapted to communicate with each other over an appropriate communication channel, such as a computer by way of example and not limitation. The external device can be used by the patient or physician to provide side effect feedback indicative of patient discomfort, for example.

According to various embodiments, the device, as illustrated and described above, is adapted to deliver neural stimulation as electrical stimulation to desired neural targets, such as through one or more stimulation electrodes positioned at predetermined location(s). Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering a vagal stimulation therapy to a vagus nerve, comprising:
 delivering a neural stimulation signal to non-selectively stimulate both afferent axons and efferent axons in the vagus nerve according to a predetermined schedule for the vagal stimulation therapy;
 selecting a value for at least one parameter for the predetermined schedule for the vagal stimulation therapy to control the neural stimulation therapy to avoid physiological habituation to the vagal stimulation therapy, the at least one parameter including at least one parameter selected from the group of parameters consisting of:
  a predetermined therapy duration parameter for a predetermined therapy period; and a predetermined intermittent neural stimulation parameter associated with on/off timing for the intermittent neural stimulation parameter.

2. The method of claim 1, wherein the at least one parameter includes the predetermined therapy duration parameter, the predetermined therapy duration parameter accounting for each neural stimulation train in the predetermined therapy period to provide an indicator for total therapy time.

3. The method of claim 2, wherein the predetermined therapy period is approximately one day.

4. The method of claim 2, wherein the predetermined therapy duration parameter represents a minimum therapy duration for the predetermined therapy period, further comprising adjusting the predetermined therapy duration parameter and limiting the adjusted therapy duration parameters to values equal or longer than the minimum therapy duration.

5. The method of claim 4, wherein the minimum therapy duration is approximately 8 hours of therapy per day.

6. The method of claim 2, wherein the at least one parameter includes the predetermined therapy duration parameter that corresponds to a therapy duration, further comprising delivering either intermittent therapy or continuous therapy during the therapy duration.

7. The method of claim 1, wherein the at least one parameter includes the predetermined intermittent neural stimulation parameter, and the intermittent neural stimulation parameter includes a predetermined duty cycle.

8. The method of claim 7, wherein the at least one parameter further includes a limit for a predetermined stimulation period, wherein the duty cycle corresponds to a percentage of the predetermined stimulation period during which the neural stimulation signal is delivered.

9. The method of claim 8, wherein the predetermined stimulation period is approximately one minute, and delivering the neural stimulation signal includes delivering the neural stimulation signal for approximately ten seconds in every stimulation period.

10. The method of claim 7, wherein the predetermined duty cycle is less than approximately 50%.

11. The method of claim 7, wherein the predetermined duty cycle is less than approximately 25%.

12. The method of claim 7, wherein the predetermined duty cycle is within a range between approximately 10% and 20%.

13. The method of claim 1, wherein the at least one parameter includes both the predetermined therapy duration parameter and the predetermined intermittent neural stimulation parameter.

14. The method of claim 1, further comprising receiving at least one therapy input or therapy feedback, and automatically adjusting an intensity of the neural stimulation using the at least one input or feedback.

15. The method of claim 14, wherein the neural stimulation signal includes a train of pulses, and adjusting the intensity includes adjusting at least one of amplitude, frequency, or pulse width of a train of pulses.

16. The method of claim 14, wherein adjusting the intensity includes adjusting the schedule within limits allowed by the at least one parameter.

17. The method of claim 1, wherein the vagal stimulation therapy includes a therapy selected from a heart failure therapy, a hypertension therapy, or a remodeling therapy.

18. The method of claim 1, further comprising varying an intensity of the neural stimulation signal according to a predetermined protocol within the predetermined schedule, wherein the predetermined protocol is selected to mimic pulsatile pressure.

19. A method, comprising:
using an external device, programming at least one neural stimulation schedule parameter for controlling a scheduled neural-stimulation therapy of an implantable neural stimulator;
delivering the scheduled neural stimulation therapy using the implantable neural stimulator, including delivering non-selective neural stimulation to both afferent and efferent axons of a vagus nerve,
wherein the at least one neural stimulation schedule parameter includes at least one parameter with a value selected to control the neural stimulation therapy to avoid physiological habituation to the vagal stimulation therapy, the at least one parameter including at least one parameter selected from the group of parameters consisting of:
at least one predetermined therapy duration parameter for a predetermined therapy period; and
at least one predetermined intermittent neural stimulation parameter associated with on/off timing for the intermittent neural stimulation parameter.

20. The method of claim 19, wherein the at least one neural stimulation schedule parameter includes both the at least one predetermined therapy duration and the at least one predetermined intermittent neural stimulation parameter, the at least one predetermined therapy duration parameter accounting for each neural stimulation train in the predetermined therapy period to provide an indicator for total therapy time, the predetermined intermittent neural stimulation parameter including a predetermined duty cycle and a predetermined stimulation period, wherein the duty cycle corresponds to a percentage of the predetermined stimulation period during which the neural stimulation signal is delivered.

21. The method of claim 19, wherein the predetermined therapy period is approximately one day, and the predetermined therapy duration parameter corresponds to approximately eight hours of therapy each day, the predetermined stimulation period is less than five minutes, and the predetermined duty cycle is less than 50%.

22. A neural stimulator, comprising:
a neural stimulation delivery system adapted to non-selectively stimulate both afferent axons and efferent axons in a vagus nerve; and
a controller operationally connected to the neural stimulation system, the controller including a neural stimulation scheduler to control neural stimulation from the neural stimulation system according to a predetermined schedule
wherein the predetermined schedule includes at least one parameter with a value selected to avoid physiological habituation to the neural stimulation, the at least one parameter including at least one parameter selected from the group of parameters consisting of:
a predetermined therapy duration parameter for a predetermined therapy period; and
a predetermined intermittent neural stimulation parameter associated with on/off timing for the intermittent neural stimulation parameter.

23. The stimulator of claim 22, wherein the neural stimulation delivery system and the controller form part of an implantable device, wherein the controller is adapted to receive programming instructions from an external device to program the at least one parameter.

24. The stimulator of claim 22, wherein the at least one parameter includes the predetermined therapy duration parameter, the predetermined therapy duration parameter accounting for each neural stimulation train in the predetermined therapy period to provide an indicator for total therapy time.

25. The stimulator of claim 22, wherein the at least one parameter includes the predetermined intermittent neural stimulation parameter, and the intermittent neural stimulation parameter includes a predetermined duty cycle.

26. The stimulator of claim 22, wherein the at least one parameter includes both the predetermined therapy duration parameter and the predetermined intermittent neural stimulation parameter.

27. The stimulator of claim 22, further comprising at least one port to receive a therapy input or therapy feedback, the controller being adapted to automatically adjust an intensity of the neural stimulation using the input or feedback.

28. The stimulator of claim 22, wherein the vagal stimulation therapy includes a therapy selected from a heart failure therapy, a hypertension therapy, or a remodeling therapy.

* * * * *

UNITED STATES PATENT AND TRADEMARK OFFICE
CERTIFICATE OF CORRECTION

| | | |
|---|---|---|
| PATENT NO. | : 8,010,198 B2 | Page 1 of 1 |
| APPLICATION NO. | : 12/231372 | |
| DATED | : August 30, 2011 | |
| INVENTOR(S) | : Imad Libbus et al. | |

It is certified that error appears in the above-identified patent and that said Letters Patent is hereby corrected as shown below:

In column 22, line 4, in Claim 19, delete "neural-stimulation" and insert -- neural stimulation --, therefor.

Signed and Sealed this
Eighteenth Day of October, 2011

David J. Kappos
*Director of the United States Patent and Trademark Office*